United States Patent
Sinz

(10) Patent No.: US 10,239,708 B2
(45) Date of Patent: Mar. 26, 2019

(54) LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventor: Achim Sinz, Waiblingen (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 15/444,625

(22) Filed: Feb. 28, 2017

(65) Prior Publication Data

US 2017/0174448 A1    Jun. 22, 2017

Related U.S. Application Data

(63) Continuation of application No. PCT/EP2015/070459, filed on Sep. 8, 2015.

(30) Foreign Application Priority Data

Sep. 9, 2014  (EP) ..................... 14184039

(51) Int. Cl.
    *B65G 54/02*    (2006.01)
    *G01N 35/04*   (2006.01)
    *B01L 9/06*    (2006.01)

(52) U.S. Cl.
    CPC ............ *B65G 54/02* (2013.01); *B01L 9/06* (2013.01); *G01N 35/04* (2013.01); *G01N 2035/0406* (2013.01); *G01N 2035/0477* (2013.01); *G01N 2035/0493* (2013.01)

(58) Field of Classification Search
    CPC ........ B65G 54/02; G01N 35/04; G01N 35/10; B01L 9/06
    See application file for complete search history.

(56) References Cited

U.S. PATENT DOCUMENTS

| | | | |
|---|---|---|---|
| 3,273,727 | A | 9/1966 | Rogers et al. |
| 3,653,485 | A | 4/1972 | Donlon |
| 3,901,656 | A | 8/1975 | Durkos et al. |
| 4,150,666 | A | 4/1979 | Brush |
| 4,395,164 | A | 7/1983 | Beltrop et al. |
| 4,544,068 | A | 10/1985 | Cohen |
| 4,771,237 | A | 9/1988 | Daley |
| 5,120,506 | A | 6/1992 | Saito et al. |
| 5,295,570 | A | 3/1994 | Grecksch et al. |
| 5,309,049 | A | 5/1994 | Kawada et al. |

(Continued)

FOREIGN PATENT DOCUMENTS

| | | |
|---|---|---|
| CN | 201045617 Y | 4/2008 |
| CN | 102109530 A | 6/2011 |

(Continued)

OTHER PUBLICATIONS

International Search Report dated Nov. 6, 2015, in Application No. PCT/EP2015/070459, 3 pages.

*Primary Examiner* — Matthew D Krcha
(74) *Attorney, Agent, or Firm* — Roche Diagnostics Operations, Inc.

(57) ABSTRACT

A laboratory sample distribution system in which a sample container carrier can be centered at a specific position is presented. A laboratory automation system with such a laboratory sample distribution system is also presented.

7 Claims, 1 Drawing Sheet

(56) References Cited

U.S. PATENT DOCUMENTS

| | | |
|---|---|---|
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mod et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 8,833,544 B2 | 9/2014 | Stoeckle et al. |
| 8,973,736 B2 | 3/2015 | Johns et al. |
| 9,097,691 B2 | 8/2015 | Onizawa et al. |
| 9,187,268 B2 | 11/2015 | Denninger et al. |
| 9,211,543 B2 | 12/2015 | Ohga et al. |
| 9,239,335 B2 | 1/2016 | Heise et al. |
| 9,423,410 B2 | 8/2016 | Buehr |
| 9,423,411 B2 | 8/2016 | Riether |
| 9,567,167 B2 | 2/2017 | Sinz |
| 9,575,086 B2 | 2/2017 | Heise et al. |
| 9,593,970 B2 | 3/2017 | Sinz |
| 9,598,243 B2 | 3/2017 | Denninger et al. |
| 9,618,525 B2 | 4/2017 | Malinowski et al. |
| 9,658,241 B2 | 5/2017 | Riether et al. |
| 9,664,703 B2 | 5/2017 | Heise et al. |
| 2002/0009391 A1 | 1/2002 | Marquiss et al. |
| 2002/0028158 A1 | 3/2002 | Wardlaw |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | Le Comte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus et al. |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1* | 2/2013 | Heise .................. B65G 54/02 414/222.13 |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0234949 A1 | 8/2014 | Wasson et al. |
| 2015/0014125 A1 | 1/2015 | Hecht |
| 2015/0166265 A1 | 6/2015 | Pollack et al. |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether et al. |
| 2015/0276778 A1 | 10/2015 | Riether et al. |
| 2015/0276782 A1 | 10/2015 | Riether |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0077120 A1 | 3/2016 | Riether |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |
| 2018/0067141 A1 | 3/2018 | Mahmudimanesh et al. |
| 2018/0074087 A1 | 3/2018 | Heise et al. |
| 2018/0106821 A1 | 4/2018 | Vollenweider et al. |
| 2018/0156835 A1 | 6/2018 | Hassan |
| 2018/0188280 A1 | 7/2018 | Malinowski |
| 2018/0210000 A1 | 7/2018 | van Mierlo |

(56) References Cited

U.S. PATENT DOCUMENTS

| | | |
|---|---|---|
| 2018/0210001 A1 | 7/2018 | Reza |
| 2018/0217174 A1 | 8/2018 | Malinowski |
| 2018/0217176 A1 | 8/2018 | Sinz et al. |
| 2018/0224476 A1 | 8/2018 | Birrer et al. |

FOREIGN PATENT DOCUMENTS

| | | | |
|---|---|---|---|
| DE | 3909786 A1 | 9/1990 | |
| DE | 102012000665 A1 | 8/2012 | |
| DE | 102011090044 A1 | 7/2013 | |
| EP | 0601213 A1 | 10/1992 | |
| EP | 0775650 A1 | 5/1997 | |
| EP | 0916406 A2 | 5/1999 | |
| EP | 1122194 A1 | 8/2001 | |
| EP | 1524525 A1 | 4/2005 | |
| EP | 2119643 A1 | 11/2009 | |
| EP | 2148117 A1 | 1/2010 | |
| EP | 2327646 A1 | 6/2011 | |
| EP | 2447701 A2 | 5/2012 | |
| EP | 2500871 A1 | 9/2012 | |
| EP | 2589966 A1 * | 5/2013 | ............ B65G 54/02 |
| EP | 2589968 A1 | 5/2013 | |
| EP | 2502675 B1 | 2/2014 | |
| EP | 2887071 A1 | 6/2015 | |
| GB | 2165515 A | 4/1986 | |
| JP | S56-147209 A | 11/1981 | |
| JP | 60-223481 A | 11/1985 | |
| JP | 61-081323 A | 4/1986 | |
| JP | S61-069604 A | 4/1986 | |
| JP | S61-094925 A | 5/1986 | |
| JP | S61-174031 A | 8/1986 | |
| JP | S61-217434 A | 9/1986 | |
| JP | S62-100161 A | 5/1987 | |
| JP | S63-31918 A | 2/1988 | |
| JP | S63-48169 A | 2/1988 | |
| JP | S63-82433 U | 5/1988 | |
| JP | S63-290101 A | 11/1988 | |
| JP | 1148966 A | 6/1989 | |
| JP | H01-266860 A | 10/1989 | |
| JP | H02-87903 A | 3/1990 | |
| JP | 03-112393 A | 5/1991 | |
| JP | 03/192013 A | 8/1991 | |
| JP | H03-38704 Y2 | 8/1991 | |
| JP | H04-127063 A | 4/1992 | |
| JP | H05-69350 A | 3/1993 | |
| JP | H05-142232 A | 6/1993 | |
| JP | H05-180847 A | 7/1993 | |
| JP | 06-26808 A | 2/1994 | |
| JP | H06-148198 A | 5/1994 | |
| JP | 06-156730 A | 6/1994 | |
| JP | 06-211306 A | 8/1994 | |
| JP | 07-228345 A | 8/1995 | |
| JP | 07-236838 A | 9/1995 | |
| JP | H07-301637 A | 11/1995 | |
| JP | H09-17848 A | 1/1997 | |
| JP | H11-083865 A | 3/1999 | |
| JP | H11-264828 A | 9/1999 | |
| JP | H11-304812 A | 11/1999 | |
| JP | H11-326336 A | 11/1999 | |
| JP | 2000-105243 A | 4/2000 | |
| JP | 2000-105246 A | 4/2000 | |
| JP | 2001-124786 A | 5/2001 | |
| JP | 2001-240245 A | 9/2001 | |
| JP | 2005-001055 A | 1/2005 | |
| JP | 2005-249740 A | 9/2005 | |
| JP | 2006-106008 A | 4/2006 | |
| JP | 2007-309675 A | 11/2007 | |
| JP | 2007-314262 A | 12/2007 | |
| JP | 2007-322289 A | 12/2007 | |
| JP | 2009-036643 A | 2/2009 | |
| JP | 2009-062188 A | 3/2009 | |
| JP | 2009-145188 A | 7/2009 | |
| JP | 2009-300402 A | 12/2009 | |
| JP | 2010-243310 A | 10/2010 | |
| JP | 2013-172009 A | 2/2013 | |
| JP | 2013-190400 A | 9/2013 | |
| SU | 685591 A1 | 9/1979 | |
| WO | 1996036437 A1 | 11/1996 | |
| WO | 2003042048 A3 | 5/2003 | |
| WO | 2007024540 A1 | 3/2007 | |
| WO | 2008133708 A1 | 11/2008 | |
| WO | 2009/002358 A1 | 12/2008 | |
| WO | 2010/042722 A1 | 4/2010 | |
| WO | 2012/170636 A1 | 7/2010 | |
| WO | 2010/087303 A1 | 8/2010 | |
| WO | 2010/129715 A1 | 11/2010 | |
| WO | 2012/158520 A1 | 11/2012 | |
| WO | 2012/158541 A1 | 11/2012 | |
| WO | 2013/152089 A1 | 10/2013 | |
| WO | 2013/169778 A1 | 11/2013 | |
| WO | 2013/177163 A1 | 11/2013 | |
| WO | 2014/059134 A1 | 4/2014 | |
| WO | 2014/071214 A1 | 5/2014 | |

* cited by examiner

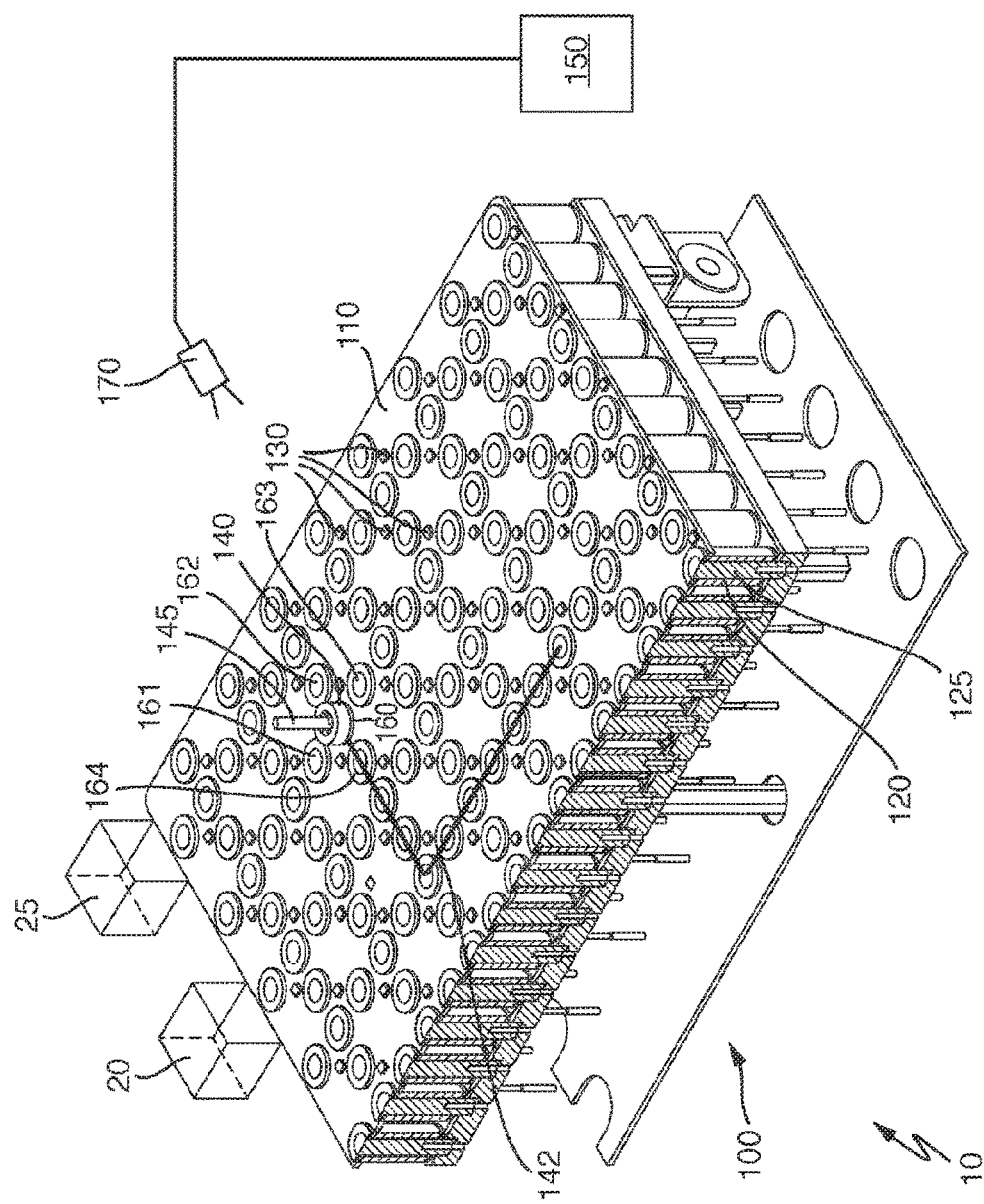

LABORATORY SAMPLE DISTRIBUTION SYSTEM AND LABORATORY AUTOMATION SYSTEM

CROSS-REFERENCE TO RELATED APPLICATIONS

This application is a continuation of PCT/EP2015/070459, filed Sep. 8, 2015, which is based on and claims priority to EP 14184039.7, filed Sep. 9, 2014, which is hereby incorporated by reference.

BACKGROUND

The present disclosure relates to a laboratory sample distribution system and to a laboratory automation system comprising such a laboratory sample distribution system.

Laboratory automation systems typically comprise a number of laboratory stations, for example pre-analytical, analytical and/or post-analytical stations, that are used in order to analyze or otherwise treat samples such as medical samples. For example, blood samples can be analyzed with such laboratory stations. Typically, such samples are contained in sample containers such as tubes made of transparent plastic material or glass material with an opening at the upper side.

In order to distribute such sample containers between the laboratory stations, a laboratory automation system typically comprises a laboratory sample distribution system that is adapted to automatically transport or distribute the sample containers between the laboratory stations. In a typical laboratory sample distribution system, in which a number of sample container carriers are adapted to each carry a sample container over a transport plane, a number of electro-magnetic actuators are positioned below the transport plane in order to drive the sample container carriers by magnetic forces. Such laboratory sample distribution systems provide an easily programmable and efficient means for automation of a laboratory automation system.

However, there is a need to further optimize a laboratory sample distribution system, especially regarding centering of sample container carriers over electro-magnetic actuators and/or in certain places.

SUMMARY

According to the present disclosure, a laboratory sample distribution system. The laboratory sample distribution system can comprise a number of sample container carriers. Each can be adapted to carry one or more sample containers and each can comprise at least one magnetically active device. The laboratory sample distribution system can also comprise a transport surface adapted to support the sample container carriers and a number of electro-magnetic actuators stationary arranged below the transport surface. The electro-magnetic actuators can be adapted to move the sample container carriers on top of the transport surface by applying a magnetic drive force to the sample container carriers. The laboratory sample distribution system can also comprise a control device. The control device can be configured to control the movement of the sample container carriers on top of the transport surface by driving the electro-magnetic actuators such that the sample container carriers move along corresponding transport paths. Each of the transport paths can end on top of a corresponding end-point electro-magnetic actuator. The control device can be configured to drive the end-point electro-magnetic actuator such that the end-point electro-magnetic actuator can apply a magnetic attractive centring force on the corresponding sample container carrier at the end of the corresponding transport path. The control device can be configured to drive all electro-magnetic actuators situated adjacent to the end-point electro-magnetic actuator such that the electro-magnetic actuators situated adjacent to the end-point electro-magnetic actuator can apply repulsive centring forces on the sample container carrier at the end of the corresponding transport path and such that at the position of the end-point electro-magnetic actuator, a sum of the magnetic repulsive centring forces in the transport plane can be zero. The magnetic attractive centring force and the magnetic repulsive centring forces can be larger than the magnetic drive force.

Accordingly, it is a feature of the embodiments of the present disclosure to provide further optimize a laboratory sample distribution system, especially regarding centering of sample container carriers over electro-magnetic actuators and/or in certain places. Other features of the embodiments of the present disclosure will be apparent in light of the description of the disclosure embodied herein.

BRIEF DESCRIPTION OF THE DRAWING

The following detailed description of specific embodiments of the present disclosure can be best understood when read in conjunction with the following drawing, where like structure is indicated with like reference numerals and in which:

FIG. 1 illustrates schematically a laboratory automation system 10 having a laboratory sample distribution system according to an embodiment of the present disclosure.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample distribution system is presented. The laboratory sample distribution system can comprise a number of sample container carriers adapted to carry one or more sample containers. Each sample container carrier can comprise at least one magnetically active device. It can further comprise a transport surface adapted to support the sample container carriers and a number of electro-magnetic actuators stationary arranged below the transport plane. The electro-magnetic actuators can be adapted to move one of the number of sample container carriers on top of the transport surface by applying a magnetic drive force to the sample container carrier.

The laboratory sample distribution system can further comprise a control device. The control device can be configured to control the movement of the sample container carriers on top of the transport plane by driving the electro-magnetic actuators such that the sample container carriers move along corresponding transport paths. The transport paths can end on top of or over a corresponding end-point electro-magnetic actuator.

The control device can further be configured to energize or drive the end-point electro-magnetic actuator such that the end-point electro-magnetic actuator can apply or exert a magnetic attractive centering force on the respective sample container carrier at the corresponding end of the transport path.

With the laboratory sample distribution system, it can be possible to center the sample container carrier especially after it has moved along its transport path. This centering can, for example, be useful in order to load a sample container in the sample container carrier or in order to unload a sample container from the sample container carrier. Having the sample container carrier centered at a certain position can allow for a smoother and faster loading or unloading process. In addition, the continuing application of the centering force may prevent the sample container carrier from inadvertently changing its position that can harm such a process.

The magnetically active devices of the sample container carriers can typically be implemented as permanent magnets. However, electromagnets can also be used.

The transport surface can typically be a flat surface on which the sample container carriers can be carried and can move.

The electro-magnetic actuators can typically be implemented as solenoids. Each solenoid can have a ferromagnetic core. Typically, axes of the solenoids can be oriented vertically and can be oriented substantially parallel to each other. The ferromagnetic cores may be magnetically coupled to neighboring ferromagnetic cores.

The control device may be implemented as a microprocessor, a microcontroller, a standard computer, an application specific integrated circuit (ASIC), a field programmable gate array (FPGA) or another programmable device. Especially, it may comprise a processor and a memory. The memory can comprise code that when executed by the processor can cause the processor to behave in a certain way.

The end-point electro-magnetic actuator can be chosen from the number of electro-magnetic actuators and can typically define the end-point of a respective transport path. In typical implementations, the end-point electro-magnetic actuator can be situated in the vicinity to a laboratory station or in the vicinity to sample container loader or unloader.

The control device can be configured to drive a number of electro-magnetic actuators situated adjacent to the end-point electro-magnetic actuator such that the electro-magnetic actuators situated adjacent to the end-point electro-magnetic actuator can apply repulsive centering forces on the sample container carrier at the end of the transport path. This can further assist centering of the sample container carrier at the end-point electro-magnetic actuator. The repulsive centering forces can be applied in addition to the attractive centering force at the same time. The repulsive centering forces can especially be used in order to apply forces in specific directions with defined strengths in order to correct for deviations.

The magnetic attractive centering force and the magnetic repulsive centering forces can be larger than the magnetic drive force. This can allow for a preferred holding of the sample container carrier at its position with a force that can prevent inadvertent movement of the sample container carrier.

The control device can be configured to energize or drive all electro-magnetic actuators situated adjacent to the end-point electro-magnetic actuator. This can allow for a specifically high centering force.

The control device can be configured to energize or drive all electro-magnetic actuators situated adjacent to the end-point electro-magnetic actuator such that at the position of the end-point electro-magnetic actuator a sum of the magnetic repulsive centering forces in transport plane direction can be zero. This can allow for a preferred centering of the sample container carrier without a resulting force at the position of the end-point electro-magnetic actuator, meaning that forces that would have to be applied in order to move the sample container carrier in any direction can be at a maximum. The just described situation can also mean that no resulting magnetic drive force can be caused by the magnetic repulsive centering forces. This can also prevent inadvertent movement of the sample container carrier due to the forces applied by the electro-magnetic actuators.

According to an implementation, the control device can be communicatively connected with a position detection device. The position detection device can be configured to detect a position of the sample container carrier and to deliver a position indicating signal to the control device. The control device can further be configured to adapt the magnetic repulsive centering forces, using the position indicating signal, such that the sample container carrier can be centered over the end-point electro-magnetic actuator.

With this implementation, the centering forces can be applied according to the actual position of the sample container carrier as detected by the position detection device. This can allow for a very exact positioning at a certain position where it can be intended to center the sample container carrier. The position detection device may, for example, be a camera with a system that can be adapted to analyze images.

According to an implementation, the control device can be configured to drive a selection of electro-magnetic actuators during movement of the sample container carrier such that the selection of electro-magnetic actuators can apply a magnetic repulsive stabilization force on the sample container carrier. This can allow for a stabilization of the sample container carrier transport path during movement. The repulsive stabilization forces can prevent the sample container carrier from leaving its intended path while moving.

According to an implementation, the control device can be configured to drive a number of electro-magnetic actuators situated adjacent to the end-point electro-magnetic actuator such that the number of electro-magnetic actuators situated adjacent to the end-point electro-magnetic actuator can exert a magnetic repulsive braking force on the sample container carrier while it is still moving. This can allow for slowing down the sample container carrier by the repulsive force. This can prevent the sample container carrier from moving over its intended end-point electro-magnetic actuator and can allow for a smooth and fast braking of the sample container carrier at the end of its path.

The invention can further relate to a laboratory automation system, comprising a number of a pre-analytical, analytical and/or post-analytical laboratory stations, and a laboratory sample distribution system as described above adapted to distribute the sample container carriers and/or sample containers between the stations. The laboratory stations may be arranged adjacent to the laboratory sample distribution system.

Pre-analytical stations may be adapted to perform any kind of pre-processing of the samples, the sample containers and/or the sample container carriers.

Analytical stations may be adapted to use the sample or part of the sample and a reagent to generate a measuring signal, the measuring signal indicating if and in which concentration, if any, an analyte exists.

Post-analytical stations may be adapted to perform any kind of post-processing of the samples, the sample containers and/or the sample container carriers.

The pre-analytical, analytical and/or post-analytical stations may comprise at least one of a decapping station, a recapping station, an aliquot station, a centrifugation station, an archiving station, a pipetting station, a sorting station, a tube type identification station, and a sample quality determining station.

Referring initially to FIG. 1, FIG. 1 shows a laboratory automation system 10 according to an embodiment. The laboratory automation system 10 can comprise a first analytical station 20, a second analytical station 25 and a laboratory sample distribution system 100. The analytical stations 20, 25 can each be adapted to perform certain analytical tasks with samples contained in sample containers. The laboratory sample distribution system 100 can be adapted to move sample containers to and from the analytical stations 20, 25.

The sample distribution system 100 can comprise a transport surface 110. Below the transport surface 110, a number of electro-magnetic actuators 120, 160, 161, 162, 163, 164 can be arranged. Each electro-magnetic actuator 120, 160, 161, 162, 163, 164 can have a ferromagnetic core 125. The electro-magnetic actuators 120, 160, 161, 162, 163, 164 can be adapted such that they can move a sample container carrier over the transport surface 110.

Below the transport surface 110, there can further be arranged a plurality of Hall-sensors 130 that can be used in order to determine respective positions of sample container carriers.

Typically, a plurality of sample container carriers can be positioned on the transport surface 110. In FIG. 1, an exemplary sample container carrier 140 is shown. The sample container carrier 140 can hold a sample container 145 and can further comprise a permanent magnet positioned inside the sample container carrier 140 so that it may not be visible in FIG. 1.

The sample distribution system 100 can further comprise a control device 150. The control device 150 can be adapted to control movement of the sample container carrier 140.

The sample container carrier 140 can already have moved along a transport path 142. The transport path 142 can extend over a plurality of electro-magnetic actuators 120, 160, 164. As long as the sample container carrier 140 moves along the transport path 142, the control device 150 can drive the electro-magnetic actuators 120, 160, 164 such that the sample container carrier 140 can be pulled from each position above an electro-magnetic actuator 120, 164 to the next.

In order to stabilize movement, electro-magnetic actuators 120 immediately adjacent to the transport path 142, especially those electro-magnetic actuators 120 that are arranged in lines parallel to the respective transport path in which only half the number of electro-magnetic actuators 120 are arranged compared with the line on which the transport path 142 extends, can be energized by the control device 150 such that they can exert a repulsive force on the sample container carrier 140.

The electro-magnetic actuator 160 at the end of the transport path 142 may be called end-point electro-magnetic actuator 160. After the sample container carrier 140 has reached the end-point electro-magnetic actuator 160, the end-point electro-magnetic actuator 160 can be driven by the control device 150 such that it can exert an attractive centering force on the sample container carrier 140. The centering force can be greater than a drive force exerted by electro-magnetic actuators 120 that is intended to drive the sample container carrier 140 along the transport path 142.

Before the sample container carrier 140 reaches the end-point electro-magnetic actuator 160, an adjacent electro-magnetic actuator 162 that is located in a possible extension of the transport path 142 can be driven by the control device 150 such that it can exert a repulsive force on the sample container carrier 140. This repulsive force can be a brake force that can be used in order to smoothly and quickly brake the sample container carrier 140 so that it can stop over the end-point electro-magnetic actuator 160. After the sample container carrier 140 has stopped over the end-point electro-magnetic actuator 160, three further adjacent electro-magnetic actuators 161, 163, 164 can also be driven by the control device 150 such that they can exert repulsive forces on the sample container carrier 140 that can sum to a vanishing force at the intended position.

The laboratory sample distribution system 100 can further comprise a position detection device 170 embodied as a camera that can be connected with the control device 150. The camera 170 can be adapted to exactly determine the position of the sample container carrier 140 on the transport surface 110. If the sample container carrier 140 is not exactly centered at the position where it should be centered, the camera 170 can detect such a deviation and report it to the control device 150. The control device 150 can then adapt the repulsive forces of the electro-magnetic actuators 161, 162, 163, 164 adjacent to the end-point electro-magnetic actuator 160 such that a correction force can be applied to the sample container carrier 140. The correction force can center the sample container carrier 140 exactly at the intended position.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A laboratory sample distribution system, the laboratory sample distribution system comprising:
   a number of sample container carriers, each being adapted to carry one or more sample containers and each comprising at least one magnetically active device;
   a transport surface adapted to support the sample container carriers;
   a number of electro-magnetic actuators stationary arranged below the transport surface, the electro-magnetic actuators adapted to move the sample container carriers on top of the transport surface by applying a magnetic drive force to the sample container carriers; and a control device, wherein the control device is configured to control the movement of the sample container carriers on top of the transport surface by driving the electro-magnetic actuators such that the sample container carriers move along corresponding transport paths, wherein each of the transport paths ends on top of a corresponding end-point electro-magnetic actuator, wherein the control device is configured to drive the end-point electro-magnetic actuator such that the end-point electro-magnetic actuator applies a magnetic attractive centring force on the corresponding sample container carrier at the end of the corresponding transport path, wherein the control device is configured to drive all electro-magnetic actuators situated adjacent to the end-point electro-magnetic actuator such that the electro-magnetic actuators situated adjacent to the end-point electro-magnetic actuator apply repulsive centring forces on the sample container carrier at the end of the corresponding transport path and such that at the position of the end-point electro-magnetic actuator, a sum of the magnetic repulsive centring forces in the transport plane is zero, and wherein the magnetic attractive centring force and the magnetic repulsive centring forces are larger than the magnetic drive force.

2. The laboratory sample distribution system according to claim 1, wherein the control device is communicatively connected to a position detection device and wherein the position detection device is configured to detect a position of the sample container carrier and to provide a position indicating signal to the control device.

3. The laboratory sample distribution system according to claim 2, wherein the control device is configured to adapt the magnetic repulsive centring forces using the position indicating signal such that the sample container carrier is centred over the end-point electro-magnetic actuator.

4. The laboratory sample distribution system according to claim 1, wherein the control device is configured to drive a selection of electro-magnetic actuators during movement of the sample container carrier such that the selection of electro-magnetic actuators applies a magnetic repulsive stabilization force on the sample container carrier.

5. The laboratory sample distribution system according to claim 1, wherein the control device is configured to drive the number of electro-magnetic actuators situated adjacent to the end-point electro-magnetic actuator such that the number of electro-magnetic actuators situated adjacent to the end-point electro-magnetic actuator exert a magnetic repulsive braking force on the sample container carrier while it is still moving.

6. A laboratory automation system, the laboratory automation system comprising:

a number of laboratory stations; and a laboratory sample distribution system according to claim 1 adapted to distribute sample containers between the laboratory stations.

7. The laboratory automation system according to claim 6, wherein the number of laboratory stations are pre-analytical, analytical and/or post-analytical stations.

* * * * *